(12) United States Patent
Friedman

(10) Patent No.: US 7,456,223 B2
(45) Date of Patent: *Nov. 25, 2008

(54) TREATMENT OF BRUXISM

(76) Inventor: Mark H. Friedman, 2 Overlook Rd., Scarsdale, NY (US) 10583

( * ) Notice: Subject to any disclaimer, the term of this patent is extended or adjusted under 35 U.S.C. 154(b) by 530 days.

This patent is subject to a terminal disclaimer.

(21) Appl. No.: 10/963,310

(22) Filed: Oct. 12, 2004

(65) Prior Publication Data

US 2006/0078511 A1  Apr. 13, 2006

(51) Int. Cl.
*A61K 31/13* (2006.01)
*A61K 31/19* (2006.01)
*A61K 31/685* (2006.01)
*A61K 31/12* (2006.01)

(52) U.S. Cl. .................. 514/662; 514/78; 514/570; 514/221; 514/681; 514/944

(58) Field of Classification Search ................ None
See application file for complete search history.

(56) References Cited

U.S. PATENT DOCUMENTS

| 5,654,337 A | * | 8/1997 | Roentsch et al. | ............ 514/570 |
| 5,837,289 A | * | 11/1998 | Grasela et al. | ............ 424/484 |
| 6,164,278 A | * | 12/2000 | Nissani | ............ 128/848 |
| 2003/0125661 A1 | * | 7/2003 | Yerushalmy | ............ 604/66 |

* cited by examiner

*Primary Examiner*—Frederick Krass
*Assistant Examiner*—Lezah Roberts
(74) *Attorney, Agent, or Firm*—Evelyn M. Sommer

(57) ABSTRACT

A composition and its use for local percutaneous delivery of a drug, in particular a muscle relaxant, more particularly cyclobenzaprine present in an amount of about 1 to about 10% by weight of the composition in an organogel cream are disclosed. The composition is applied directly to the skin over accessible muscles of mastication from which it is rapidly absorbed through the skin to provide control of conditions such as bruxism and tooth clenching. The composition can also be applied to the skin overlying these muscles to control muscle hyperactivity (spasm) and/or trigger points, from other causes. The composition can be formulated to include another active agent such as a non-steroidal anti-inflammatory, for example ketoprofen.

11 Claims, 4 Drawing Sheets

A. Masseteric Tendon.
B. Deep Vertical Masseteric Fibers.
C. Muscle Belly.
D. Area Lateral To The TMJ.

TREATMENT OF BRUXISM

RELATED APPLICATION

This application is related to application Ser. No. 09/495,690, issued to U.S. Pat. No. 6,632,843 on Oct. 14, 2003.

FIELD OF THE INVENTION

This invention relates to the use of a composition for the local percutaneous delivery of at least one muscle relaxant formulated in an organogel cream.

In the preferred embodiment of the invention, the composition is formulated with the muscle relaxant, cyclobenzaprine, present in an amount of about 1 to 14% by weight of the composition. The composition is applied by the patient, directly to the skin, over accessible muscles of mastication (masseter and temporalis). The composition is rapidly absorbed through the skin to provide control of muscle tension and relief from any pain resulting in and from bruxism (tooth grinding) and tooth clenching (isometric muscle contraction). In accordance with another embodiment, the composition can be formulated to include an additional pharmaceutically active agent such as a non-steroidal anti-inflammatory drug, for example ketoprofen or other similarly active agent. Other pharmacologically active substances that can be added, include for example an anti-anxiety compound such as diazepam.

BACKGROUND OF THE INVENTION

Bruxism (tooth grinding when not masticating or swallowing) and tooth clenching (isometric muscle contraction with the teeth in contact) are common functional jaw disturbances.

The isometric contraction produced during clenching is even more tiring to the muscles than the isotonic contraction produced during bruxism. However, bruxing forces are considerable. The volume of the sound produced during grinding is substantial and is difficult to simulate voluntarily. This excitation of the jaw closing muscles appears to serve as a tension-relieving mechanism Some individuals are more susceptible to environmental stress, and respond by increased jaw muscle tension, either at night or with daytime clenching. It has been postulated that the protective mechanism in these individuals has been dulled down. Experimental evidence has shown that in addition to discomfort, damage accompanies such muscular hyperactivity.

Para-functional oral habits, particularly bruxism, and tooth clenching as well as myofacial pain are common components of temporomandibular joint (TMJ) dysfunction. TMJ disorders are estimated to affect from 10 to 30 million Americans with approximately one million new patients diagnosed yearly. The majority of the sufferers are women, ages 20 to 40. It has been demonstrated that tooth clenching or tooth grinding in response to stressful life situations is associated with or may actually induce depression, anxiety, frustration and chronic pain. These symptoms are more marked in patients with TMJ problems than in control subjects. The regular repetitive side-to-side tooth contacts of bruxism differ from the haphazard pattern observed during mastication. Bruxism or clenching at night is often totally beyond the patient's awareness. A classic presentation is pain in front of and just below the tragus, with radiation to the ear, lower jaw, cheek and temple. Pain is usually worse in the morning and may occur in cyclical episodes. In response to questioning, these individuals often describe (1) orofacial or jaw pain and other symptoms on arising, (2) posterior tooth soreness on arising, (3) teeth pressed together on awakening, and (4) jaw "tiredness" during chewing. Typical wear facets and/or worn teeth can be seen in strong bruxers, but not in those who clench. Nocturnal monitoring of masseteric electromyographic (EMG) activity in bruxers showed marked increases of EMG activity (bruxism) during periods of life situational stress. These habits abuse the masticatory muscles, especially the masseter, and result in muscle dysfunction, i.e. muscle spasm and trigger points. Muscle spasm is the commonest manifestation of musculoskeletal pathology, and can be defined as a prolonged continuous contraction of muscle. Trigger points are small., ischemic, tender points in the involved muscle and its associated area caused by abnormal functioning (overloading) of the muscle. The trigger points can refer pain and other symptoms, especially jaw tiredness. Trigger points are undetectable by the usual muscle tests, such as application of maximal resistance to the muscle. Muscles in spasm respond to these tests by demonstrating pain or other symptoms. Due to a lowered skin resistance (impedance) over the point, trigger points can be verified by various electronic detectors. In addition to referring pain, they perpetuate muscle tenderness, and prevent full muscle lengthening (relaxation). In bruxers or clenchers, multiple trigger points are almost always found in the deep vertical fibers of the masseter muscle, just under the temporomandibular joint, and often in the posterior belly of the digastric and stylohyoid muscles, anterior and inferior to the ear lobe(s). Trigger points in these muscles often refer symptoms, such as congestion, pain, and tinnitus to the ears, as well as giving rise to swallowing difficulties, i.e., eustachian tube dysfunction This is often confusing in treatment, since, in these cases, objective signs of ear dysfunction are absent.

Bruxism and/or clenching can be initiated by systemic, psychological, occupational and occlusal factors. Often, a combination of general and local factors influencing each other set up a vicious cycle. Standard treatment for the above parafunctional habits generally consists of one or more of the following; physical therapy and namely prescribed exercises, massage, application of moist heat, or cold in the form of ice packs, behavior modification, medication taken orally including non-steroidal anti-inflammatories, muscle relaxants, tricyclic antidepressants, tranquilizers or anti-anxiety drugs. Behavior modification, with stress reduction as its goal, generally consists of counseling on life style and relaxation therapy and/or biofeedback. Biofeedback uses equipment to measure biologic activity, e.g., surface electromyography to measure muscle activity. A "feed back loop" allows the patient to receive immediate information (feedback). The patient, guided by this information, is then trained to reduce excessive muscular activity by appropriate thought processes (U.S. Pat. Nos. 6,117,092, 6,270,466). Various devices have been produced for preventing bruxism, and they include those which electrically stimulate the jaw (U.S. Pat. No. 4,669,477), the neck (U.S. Pat. No. 4,715,367), the lip (Clark, G. T. et al CDA Journal 21(1):19-30, 1993), the mouth (U.S. Pat. Nos. 4,995,404; 6,490,520), or tooth (U.S. Pat. No. 5,553,626) and those which use mild aversive shocks upon detecting the occurrence of bruxism (U.S. Pat. No. 4,715,367), and those which alarm the user upon detection of bruxism (U.S. Pat. Nos. 4,220,142; 4,976,618; 4,979,516; 4,989,616; 4,995,404; 5,078,153; 5,586,562; 6,164,278). Control of bruxism or clenching by medication usually involves muscle relaxants, such as diazepam (U.S. Pat. No. 6,638,241) or cyclobenzaprine (U.S. Pat. No. 6,632,843). These medications when taken orally are associated with side effects; particularly sedation, and dependency, in the case of diazepam can be a problem. Other prescribed medications resembling muscle relaxants, such as Esgic (butalbital, acetaminophen and caffeine), have generalized depressive effects on the central nervous system and can be addictive. Recently, neurotoxins such as botulinum toxin have been used to treat myofacial pain and bruxism (U.S. Pat. No. 6,333,037). Biosensory devices have also been conceived for the automatic delivery of the medications (U.S. Pat. No. 6,638,241).

Removable dental appliances are commonly prescribed to control or eliminate these harmful oral habits (Rugh, J. D. et al *Journal of Craniomandibular Disorders* 3(4):203-210, 1989). These appliances, usually designed with flat occlusal surfaces, fit over the maxillary or mandibular teeth to prevent complete closure, since the powerful jaw closing muscles (masseter, temporalis, medial pterygoid) cannot shorten completely, they cannot contract as forcefully. Additionally, the flat occlusal surface eliminates the usual triggers, abrasive contact between irregular tooth surfaces.

Occlusal adjustments, elimination of perceived excessive tooth contact by grinding, may be effective. However if incorrect surfaces are removed, the situation may worsen. Unlike appliances, which can be modified by adding or subtracting plastic, elimination of tooth surface is irreversible.

SUMMARY OF THE INVENTION

Figure 1:
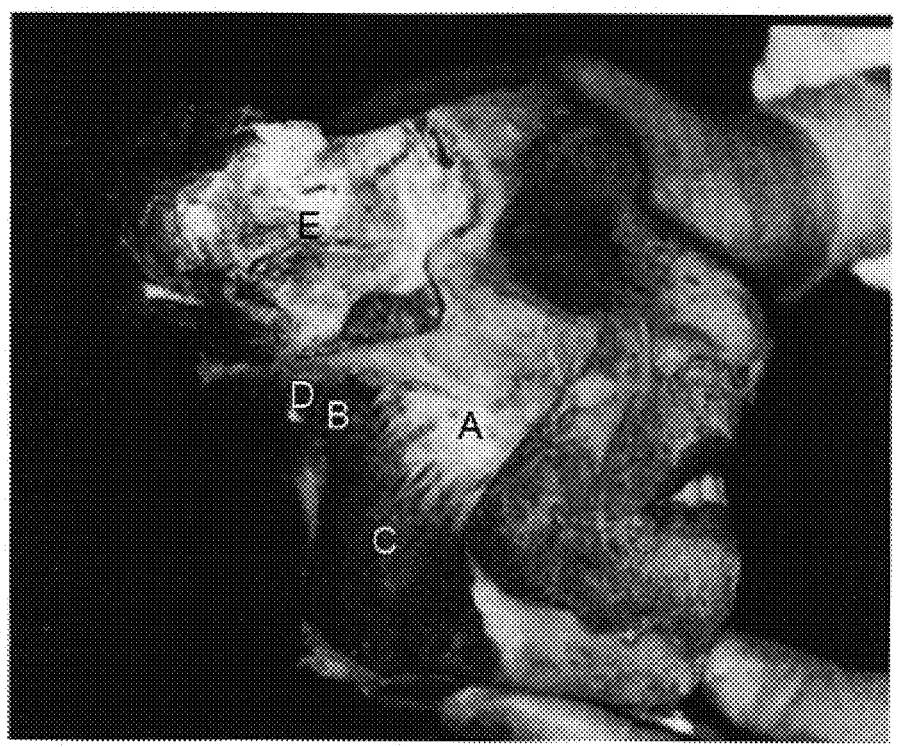
FIG. 1 illustrates the lateral aspect of the masseter muscle.
Figure 2:
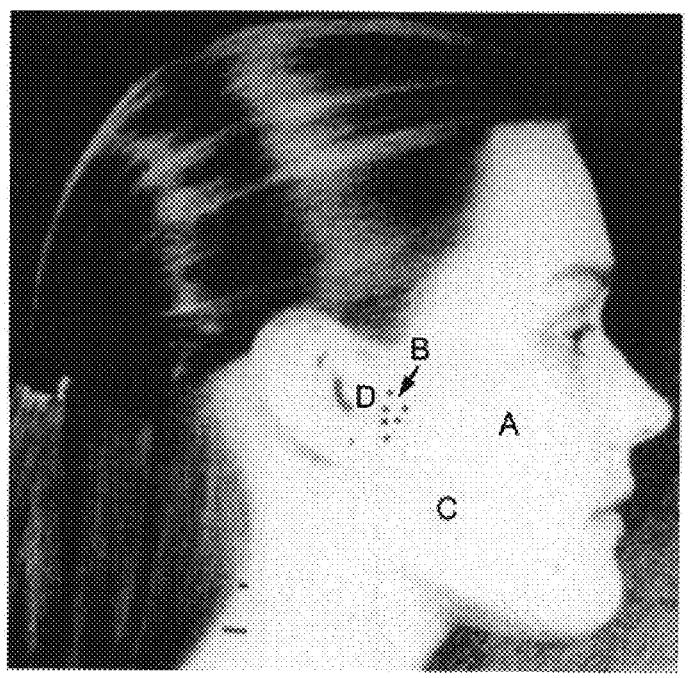
FIG. 2 illustrates the areas evidencing tenderness in a patient.
Figure 3:
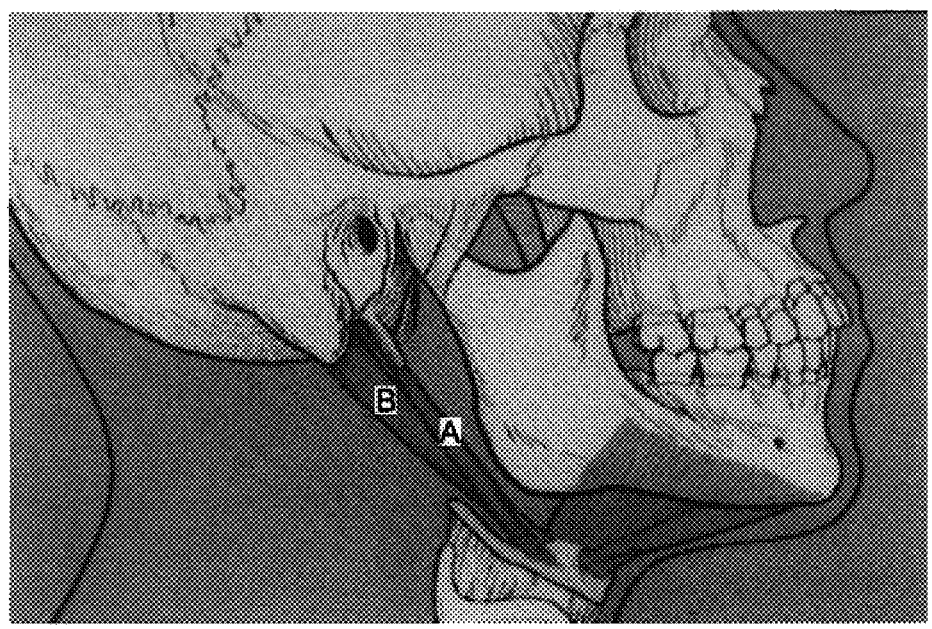
FIG. 3 illustrates the anatomy of the digastric muscle.
Figure 4:
FIG. 4 illustrates the area of treatment in a patient.

This invention relates to the use of compositions adapted to be used in the treatment of temporomandibular disorders, including bruxism, tooth grinding, tooth clenching and various ear symptoms including, congestion, swallowing difficulties, tinnuitis, and pain referred from adjacent muscles.

In accordance with the invention the compositions are applied topically onto the intact skin over accessible muscles, i.e., masseter and temporalis for local subcutaneous delivery of a muscle relaxant and namely cyclobenzaprine. The compositions can include more than one active agent and are to be administered to a patient who might benefit from the differing properties of such a formulation. Thus, the composition may be formulated to comprise other pharmaceutically active agents in addition to the muscle relaxant. Such agents include a non-steroidal anti-inflammatory, preferably ketoprofen, or an anxiolytic agent such as diazepam. The composition, formulated as a cream using lecithin organogel as the delivery vehicle, is applied by the patient onto the intact skin overlying accessible muscles of mastication, i.e., masseter, temporalis. Similarly application of the composition to these or other muscles may be used to control muscle spasm or hyperactivity. It may be applied to tender spots known as trigger points in the involved muscle and associated area. Once the formulations have been prepared, use of the composition is a simple matter of applying the formulation to the affected areas where transdermal delivery of the pharmaceutically active agent(s) is desired. The amount of cream applied, about one gram, is used to cover an area the size of two fingers (about one inch by two inches). The advantages of topical administration include use of lower doses of active agents, avoidance of the gastrointestinal tract and hepatic first by-pass biotrans formation and metabolism, and delivery of the drug to the a specific area (local) versus systemic distribution of the drug.

The compositions for transcutaneous delivery of pharmaceutically active agent(s) are formulated in organogel. This gel comprises a biocompatible organic solvent, a polar lipid, a biocompatible surfactant, water, urea and the pharmaceutically active substance(s). The polar lipid is preferably lecithin, the biocompatible organic solvent is preferably isopropyl myristate and the surfactant preferably is docusate sodium. Preferred composition comprise preferably lecithin 10-30%, isopropyl myristate 10-30%, urea 5-20%, water 30-60% and surfactant 10-20%. (All percentages are weight percent of the composition.) After formulation of the composition with the pharmaceutically active agent, and adjustment of the pH to the desired range, the formulation thickens and forms a gel suitable for topical administration. The final pH should be in the range of 6.0 to 7.0. The appropriate pH is obtained by adjusting the composition with aqueous NaOH. Depending on the chemical properties, for example the solubility characteristics of the pharmaceutically active agent the steps in compounding the composition may vary slightly. Some agents may require some heating before a consistent mixture may be achieved. The active compound is added to the mixture of the polar lipid and organic solvent. The mixture may be warmed before adding the active compound if required for solubilizing the active agent. Thorough mixing is accomplished by stirring.

Cyclobenzaprine HCl (Flexeril, Merck) relieves muscle spasm of local origin without interfering with muscle function (Katz, W., et al. *Clinical Therapeutics* 10:216-228, 1988).

It is expected that a similarity between the effects of cyclobenzaprine and the structurally related tricyclic antidepressants e.g. amitryptyline will exist. Cyclobenzaprine is a 5-HT2 receptor antagonist and its muscle relaxant effect is due to inhibition of serotonergic neurons. Cyclobenzaprine significantly improves the signs and symptoms of skeletal muscle spasm. The clinical response includes improvement in local pain and tenderness and increased range of motion. Clinical improvement is often observed as early as during the first 20 minutes of application. When taken orally, cyclobenzaprine is eliminated slowly with a half life as long as one to three days it is highly bound to plasma proteins, is metabolized primarily to glucuronide like conjugates and is excreted, primarily through the kidneys. First pass metabolism is avoided by topical administration Diazepam (Valium, Roche) which can be given concomitantly with Flexeril has been indicated for the management of anxiety disorders or for the shorterm relief of the symptoms of anxiety, or tension associated with stress. It has been found to be a useful adjunct for the relief of skeletal muscle spasm.

Ketoprofen (Orudis, Wyeth) is another example of a drug which can be co-administered with Flexeril a non-steroidal anti-inflammatory drug with analgesic and antipyretic properties. Ketoprofen has been shown to have inhibitory effects on prostaglandin and Icukotriene synthesis, to have anti-bradykinin activity as well as to have lysosomal membrane stabilizing activity. When taken orally the drug is bound to plasma proteins and is excreted in the urine mainly as glucuronide like conjugates.

Formulations containing the above agents are prepared so that cyclobenzaprine is present, expressed by weight percentage of the composition, in an amount of about 1.0-14%; ketoprofen about 5.0-10%; and diazepam about 0.5-1.0%; of course, both diazepam ketoprofen need not be present simultaneously.

The composition (organogel plus the pharmaceutical active agent) is applied by the patient, usually at bedtime; it can be used at other times of the day if necessary. The usual area of application is roughly that covered by two fingers, (an area of about one inch by two inches) and the amount of composition delivered would be about 1 ml (about one gram of composition).

I claim:

1. A method for treating tooth grinding and tooth clenching in a patient having such condition which comprises topically applying directly onto the skin overlying accessible muscles of mastication (masseter and temporalis) for absorption through the skin and local subcutaneous delivery thereto of, a therapeutically effective amount of a composition comprising about 1 to 14% by weight of cyclobenzaprine in a pharmaceutically acceptable carrier.

2. Method according to claim 1 wherein said carrier is an organogel cream.

3. Method according to claim 2 wherein said organogel cream comprises lecithin, isopropyl myristate, urea, a surfactant and water.

4. Method according to claim 1 wherein said composition additionally contains at least one nonsteroidal anti-inflammatory drug.

5. Method according to claim 4 wherein said nonsteroidal anti-inflammatory drug is ketoprofen.

6. Method according to claim 1 wherein said composition additionally contains an anti-anxiety drug.

7. Method according to claim 6 wherein said anti-anxiety drug is diazepam.

8. Method according to claim 1 wherein said composition is applied in an amount of about one (1) gram to a skin area of about 1 to 2 inches.

9. Method according to claim 1 wherein ketoprofen is additionally present in an amount of about 5.0-10% by weight.

10. Method according to claim 1 wherein diazepam is additionally present in an amount of 0.5-1% by weight.

11. Method according to claim 1 wherein said cyclobenzaprine is present in an amount of about 1 to 10% by weight of the composition.

* * * * *